United States Patent [19]

Okuhara et al.

[11] Patent Number: 4,813,537
[45] Date of Patent: Mar. 21, 1989

[54] PACKAGE FOR STORING SUTURES

[75] Inventors: Makoto Okuhara, Chiba; Yasumi Ishida, Saitama, both of Japan

[73] Assignee: Nippon Shoji Kabushiki Kaisha, Osaka, Japan

[21] Appl. No.: 147,396

[22] Filed: Jan. 25, 1988

[30] Foreign Application Priority Data

Jan. 26, 1987 [JP] Japan .................. 62-9671[U]

[51] Int. Cl.⁴ .............................. A61L 15/00
[52] U.S. Cl. .................... 206/63.5; 206/380; 206/388
[58] Field of Search .............. 206/63.3, 63.5, 363, 206/380, 382, 388, 476, 222

[56] References Cited

U.S. PATENT DOCUMENTS

| | | | |
|---|---|---|---|
| 2,617,523 | 11/1952 | Zoller | 206/63.3 |
| 3,062,372 | 11/1962 | Egler et al. | 206/63.3 |
| 3,163,288 | 12/1964 | Arvidsson | 206/63.3 |
| 3,444,994 | 5/1969 | Kaepernik et al. | 206/63.3 |
| 3,939,969 | 2/1976 | Miller et al. | 206/63.3 |
| 4,063,638 | 12/1977 | Marwood | 206/227 |
| 4,069,912 | 1/1978 | Black et al. | 206/63.3 |
| 4,555,016 | 11/1985 | Aday et al. | 206/63.3 |
| 4,572,363 | 2/1986 | Alpern | 206/63.3 |
| 4,574,957 | 3/1986 | Stead | 206/633 |

FOREIGN PATENT DOCUMENTS 2161130  1/1986  United Kingdom .............. 206/63.3

Primary Examiner—David T. Fidei
Attorney, Agent, or Firm—Frank J. Jordan; C. Bruce Hamburg; Manabu Kanesaka

[57] ABSTRACT

A suture package has a first panel and a second panel thermally bonded to form a suture compartment therebetween, the suture compartment including apertures adapted to allow pins to pass through for provisionally winding the suture around, the first panel including a stitch crosswisely produced, and the second panel has a cutaway portion which allows an upper portion of the first panel to protrude beyond the second panel as a tab whereby the user easily grasps the first panel and tears the same along the stitch. The suture is accommodated with its main portion being located within the suture compartment and with its end portions outside it.

9 Claims, 3 Drawing Sheets

FIG.5(b)  FIG.5(a)
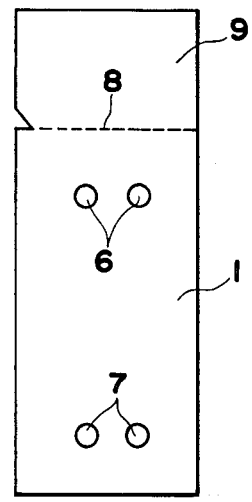
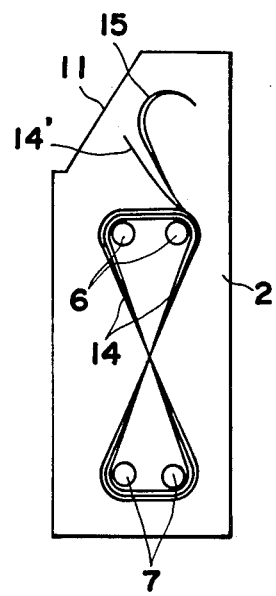
FIG.6
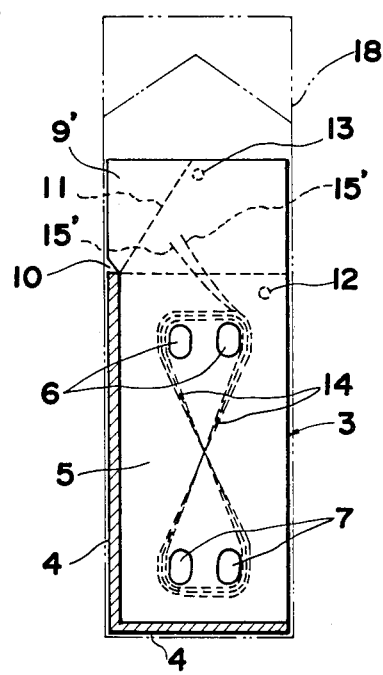

PACKAGE FOR STORING SUTURES

BACKGROUND OF THE INVENTION

1. Field of the Invention

The present invention relates to a package for storing a suture or surgical thread. More particularly, the present invention relates to a package for storing a suture in such a manner that it has no bent portion or curling tendency when it is unpacked for use, wherein the suture includes one having a needle at neither end and one having a needle at an end. In this specification the former is referred to as an unneedled suture and the latter as a needled suture which is further classified into a single needled suture and a double needled suture. However unless specified to the contrary the end portion of a suture may include an unneedled end and a needled end.

2. Description of the Prior Art

There are at least three kinds of sutures; one is unneedled, another is single-needled, and a third is double-needled. When they are stored in a package the common practice is that after a suture is cut to a given length, it is accommodated as it is wound around a plurality of pins. The package is wrapped in a plastic film, an aluminum foil or their composite sheet so as to protect the packed suture against moisture and dirt. When the packed suture is to be taken out, the package is unwrapped, and the end of the suture or the needle attached thereto is picked up through the opening of the package.

In packing a suture there are two important things to be observed; the first is to accommodate it in the package with no tangle or bent portion, and the second is to design the package in such a manner as to open readily and allow the user to pick up the packed suture smoothly.

To meet these requirements there have been made many proposals among which are disclosed in Japanese Patent Publication (unexamined) Nos. 58(1983)-149750, 59(1984)-228845 and 60(1985)-148550.

The prior art packages consist of panels folded at least in three, so as to have functionally distinguished three sections. For example, a single-needled suture is accommodated in such a manner that the wound suture and its unneedled end are located in one section, and the needle is in another. The package disclosed in the No. 60-148550 Specification has five panels connected to each other by folds. The panels consist of a suture retaining panel, a needle retaining panel, a needle covering panel, a suture covering panel and a side panel. When the suture is provided with a needle at an end, the main body of the suture is wound around pins protruded through four apertures produced in the suture retaining panel, and the needle and the part of suture adjacent to the needle are inserted in respective slits produced in the needle retaining panel. The suture covering panel is folded onto the suture retaining panel, and the needle covering panel is folded onto the suture covering panel. Finally the side panel is folded onto the needle covering panel. In this way a package is finished.

The provision of the functionally distinguished panels is advantageous in that the suture is kept safe from becoming tangled, and that it is convenient for the user when the suture is unpacked from the package. However it is labor-consuming to make as many folded panels as five, and care must be especially taken when the needle is removed out of the slit in the package. More disadvantageously the part of suture adjacent to the needle becomes bent or curls.

OBJECTS AND SUMMARY OF THE INVENTION

The present invention aims at solving the problems pointed out with respect to the prior art suture packages, and has for its object to provide an improved suture package capable of easy fabrication with the minimum number of folded panels.

Another object of the present invention is to provide an improved suture package accommodating the suture without imparting a curling tendency thereto.

Other objects and advantages of the present invention will become more apparent from the following detailed description, when taken in conjunction with the accompanying drawings which show, for the purpose of illustration only, one embodiment in accordance with the present invention.

According to the present invention there is provided a suture package which comprises:

a substrate having a first panel and a second panel thermally sealable along at least two edges thereof and at least two spots, thereby forming a suture compartment therebetween;

a pair of apertures provided in the suture compartment, each pair being spaced from each other, the apertures being adapted to allow pins to pass through for provisionally winding the suture around;

the first panel including a stitch produced along the upper edge of the suture compartment so that the first panel is readily torn along the stitch;

the second panel having a cutaway portion which allows an upper portion of the first panel to protrude beyond the second panel as a tab whereby the user easily grasps the first panel and tears the same along the stitch; and the suture compartment accommodating a main portion of a suture whereas the end portions thereof are located outside it.

BRIEF DESCRIPTION OF THE DRAWINGS

FIGS. 5(a) and (b) are front views showing the first panel and the second panel, respectively;

FIG. 6 is a front view showing a package storing a suture having no needle, and

DETAILED DESCRIPTION OF THE PREFERRED EMBODIMENT

Figure 1:
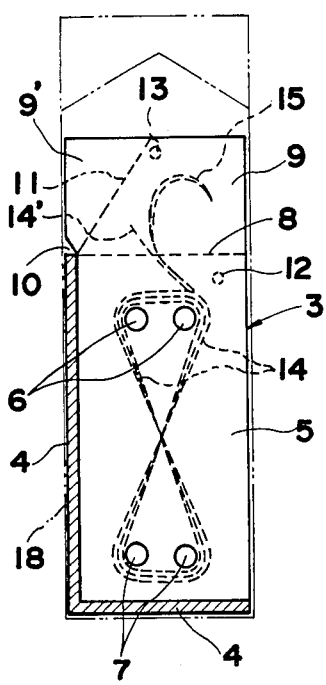
FIG. 1 is a front view showing a package embodying the present invention, the package being wrapped in a sealing film.
Figure 2:
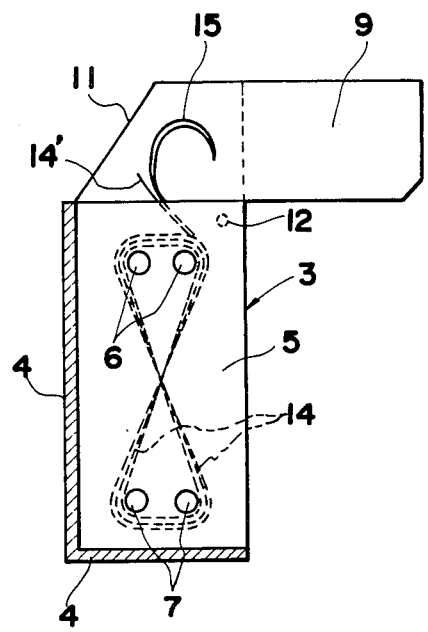
FIG. 2 is a front view showing the package of FIG. 1 when an opener section is opened.
Figure 3:
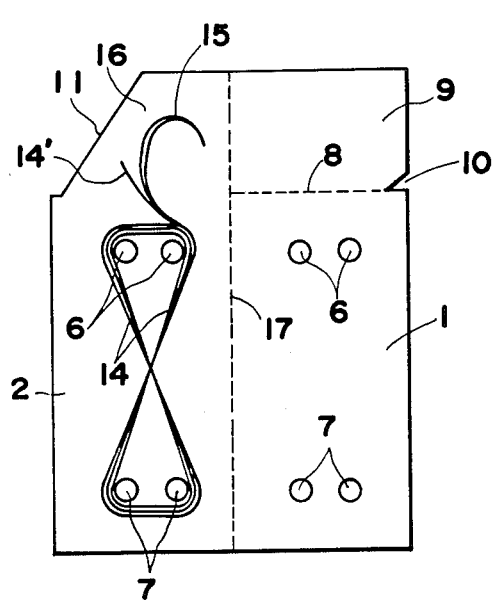
FIG. 3 is a front view showing the package of FIG. 1 in its fully unfolded state.

Referring to FIGS. 1 to 3 the package of the present invention has a first (front) panel 1 and a second (rear) panel 2 foldable along a folding line 17, hereinafter referred to as "fold", wherein the two panels 1 and 2 are made of thick paper and coated with polyethylene on their inner surfaces. The panels 1 and 2 are preferably rectangular in shape. When they are folded and overlaid on each other, their two edges crossing at right angle are thermally bonded into a substrate 3; in the illustrated embodiment one longitudinal edges and the lower edges are bonded, wherein the reference numeral 4 denotes a heat seal. There is formed a space between the panels 1 and 2, and this space provides a suture compartment 5 adapted to accommodate a suture 14. The suture compartment 5 includes two pairs of apertures 6 and 7, vertically spaced from each other, through which pins (not shown) are inserted for winding the suture 14 there around. It is possible to reduce the number of the apertures 6 and 7; for example, one above and the other below, totally two. However, it is preferred that one pair above and the other pair below, totally four apertures, are provided, which prevents the suture from becoming tangled or twisted. Actually the number of apertures is decided depending on the size of the package, and the thickness and length of the suture. The shapes of the apertures 6 and 7 are normally circular, but they can be vertically elongated so that the spacing between the pins may be adjusted to wind different lengths of sutures around the pins. The suture compartment 5 is provided with a stitch 8, along which an opener section 9 of the first panel 1 is torn as shown in FIG. 2. The stitch 8 has a tear notch 10 for facilitating the tearing of the opener section 9 along the stitch 8. The second panel 2 has a cutaway portion along an edge 11 extending diagonally from the tear notch 10. The reference numeral 9' denotes a tab projecting in the cutaway portion of the second panel 2. The user grasps the tab 9' and tears the opener section 9 along the stitch 8. The two panels 1 and 2 are additionally bonded by heat at spots 12 and 13, which are located in opposite directions to the accommodated suture end portions including the needle or needles. Thus the suture ends are secured in the package.

The suture 14 is accommodated in the suture compartment 5, wherein it is wound in the form of numeral "8" around the pins inserted through the apertures 6 and 7. The needle 15 and the end 14' of the suture 14 are located outside the suture compartment 5, that is, in an upper space between the panels 1 and 2.

The suture 14 is accommodated in the following manner:

Referring to FIG. 3 pins (not shown) are inserted through the apertures 6 and 7 in the second panel 2. The suture 14 is folded in half, or when required, in more folds; in the illustrated embodiment it is provided with a needle 15 at one end, and the other end 14' has no needle. Then it is wound around the pins in the form of numeral "8", wherein the terminal end 14' and the needle 15 are located on the inner upper side 16 of the second panel 2 as best shown in FIG. 3. Then, as shown in FIG. 1 the first panel 1 is folded along the fold 17 over the second panel 2 in such a manner that the pins pierce through the apertures 6 and 7 in the first panel 1. Finally the panels 1 and 2 are thermally bonded at 4, 12 and 13. The package is released from the pins.

Figure 4:
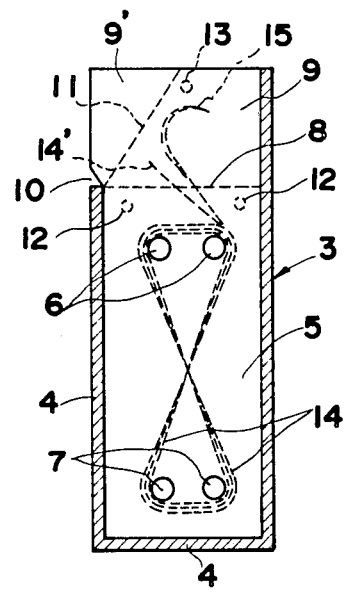
FIG. 4 is a front view showing a modified version of the package.
Figure 7:
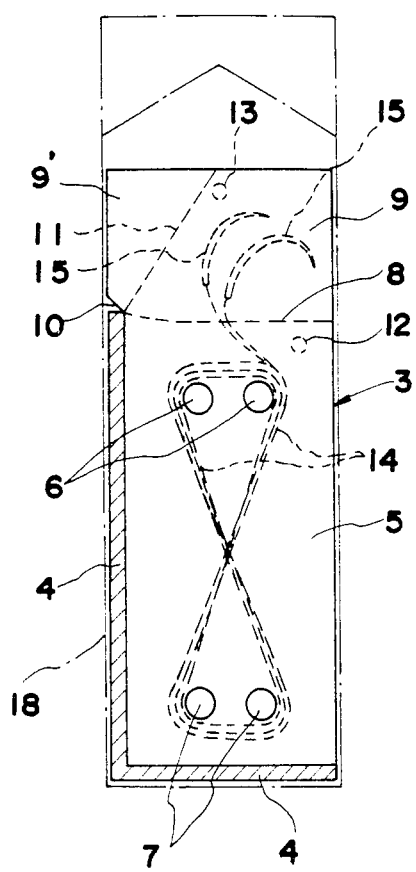
FIG. 7 is a front view, similar to FIG. 1, wherein a suture having two needles is packed in a package of the invention.

FIG. 5 shows a modified version of the package, in which the first panel 1 and the second panel 2 are separated from each other. They are thermally bonded in the same manner as mentioned above, and the finished package is the same as that shown in FIG. 4. FIG. 6 shows an example in which the suture 14 has no needle, and the both ends 15' of the suture are located in an upper space between the panels 1 and 2. FIG. 7 shows an example in which the suture 14 has two needles 15 located in an upper space between the panels 1 and 2.

The thermally sealable panels can be made of relatively stiff plastic sheet, such as polyethylene sheet, and it is possible to coat the inner sides of the panels with polyethylene or polypropylene. The package is vertically longitudinal as shown in the drawings, and the dimensional ratio of the package to the suture compartment is in the range of 3:2 to 4:3.

According to the present invention the suture is accommodated in the package safely from becoming tangled, bending and/or curling, and also it is protected against moisture and dirt. When the suture is to be unpacked the user has only to nip the tab 9' and tear the opener section 9 along the stitch 8. Then the user picks up the needle 15 and the end 14' or both ends 15'. The suture 14 has no tendency of bending or curling when it is used in a surgical operation.

What is claimed is:

1. A suture package for storing a suture therein, comprising:

a first panel including a lower section to constitute a suture compartment and having therein at least two apertures situated away from each other, an upper section to constitute an opener section, a tear line situated between the lower and upper sections, and a notch formed at one side of the tear line so that the upper section can be easily torn along the tear line when the upper section is pulled, and a second panel having a size similar to the first panel and bonded to the first panel, said second panel including a cutaway portion at an upper side portion so that when the first and second panels are bonded together, a part of the upper section of the first panel extends beyond the cutaway portion to form a tab, at least two apertures corresponding to the apertures of the first panel, said second panel being bonded to the first panel along the outer periphery except an upper portion and the cutaway portion thereof, said suture being located in the suture compartment and end portions of the suture being located in the opener section so that the suture can be easily removed from the package when the upper section of the first panel is removed.

2. A suture package according to claim 1, wherein said first and second panels are further bonded together by at least one spot adjacent the tear line inside the lower section, and at least one additional spot at the upper section so that the suture can be securely retained inside the package.

3. A suture package according to claim 1, wherein four apertures are formed at the respective first and second panels, two apertures being located adjacent to each other to form a pair, respectively.

4. A suture package according to claim 1, wherein the first and second panels are formed of a single panel, which is folded to form the first and second panels.

5. A suture package according to claim 1, wherein the inside of the package is coated with polyethylene.

6. A combination of a suture and a package for storing the suture, comprising, a package including first and second panels, said first and second panels being formed of a single panel folded along a center thereof to thereby constitute the first and second panels, said first panel including a lower section to constitute a suture compartment and having therein at least two apertures situated away from each other, an upper section to constitute an opener section, a tear line situated between the lower and upper sections, and a notch formed at a side of the tear line so that the upper section can be easily torn along the tear line when the upper section is pulled, and said second panel including a cutaway portion at an upper side portion so that when the first and second panels are folded, a part of the upper section of the first panel extends beyond the cutaway portion to form a tab, at least two apertures corresponding to the apertures of the first panel, said first and second panel being bonded together along the outer periphery except an upper portion and the cutaway portion thereof, and a suture having end portions, said suture being located in the suture compartment and the end portions being located in the opener section so that the suture can be easily removed from the package when the upper section of the first panel is removed.

7. A combination according to claim 6, wherein said first and second panels are further bonded together by at least one spot adjacent the tear line inside the lower section, and at least one additional spot at the upper section so that the suture can be securely retained inside the package.

8. A combination according to claim 7, wherein the suture is equipped with at least one needle at an one end portion thereof.

9. A combination according to claim 8, wherein the suture is equipped with two needles at both end portions.

* * * * *